(12) United States Patent
Nishino et al.

(10) Patent No.: US 7,538,212 B2
(45) Date of Patent: May 26, 2009

(54) INTERMEDIATE FOR CARBAPENEM COMPOUND FOR ORAL ADMINISTRATION AND PROCESS FOR PRODUCING THE SAME

(75) Inventors: Keita Nishino, Hyogo (JP); Teruyoshi Koga, Hyogo (JP)

(73) Assignee: Kaneka Corporation, Osaka (JP)

( * ) Notice: Subject to any disclaimer, the term of this patent is extended or adjusted under 35 U.S.C. 154(b) by 365 days.

(21) Appl. No.: 10/533,868

(22) PCT Filed: Nov. 13, 2003

(86) PCT No.: PCT/JP03/14419

§ 371 (c)(1),
(2), (4) Date: Apr. 24, 2006

(87) PCT Pub. No.: WO2004/043973

PCT Pub. Date: May 27, 2004

(65) Prior Publication Data

US 2006/0252929 A1    Nov. 9, 2006

(30) Foreign Application Priority Data

Nov. 13, 2002    (JP)    ............................. 2002-330127

(51) Int. Cl.
*C07F 9/572*    (2006.01)
*C07D 205/08*    (2006.01)

(52) U.S. Cl. ...................................... 540/200; 540/302

(58) Field of Classification Search ................. 540/302, 540/200
See application file for complete search history.

(56) References Cited

U.S. PATENT DOCUMENTS

2006/0009442 A1*    1/2006    Nishino et al. ............... 514/192

FOREIGN PATENT DOCUMENTS

EP    0 188 816 A1    7/1986
(Continued)

OTHER PUBLICATIONS

Mori, Chemical and pharmaceutical bulletin 2000, vol. 48, No. 1, pp. 126-130.*
(Continued)

*Primary Examiner*—Mark L Berch
(74) *Attorney, Agent, or Firm*—Brinks Hofer Gilson & Lione

(57) ABSTRACT

The present invention provides a novel intermediate represented by formula (1), (3), or (4) for efficiently producing a 1β-methylcarbapenem compound for oral administration, and a process for producing the intermediate. That is, the present invention provides a process for producing a novel β-lactam compound represented by formula (4), the process including allowing a β-lactam compound represented by formula (5) as a starting material to react with a compound represented by formula (6) in the presence of a base to obtain a novel β-lactam compound represented by formula (1), protecting the hydroxyl group, subsequently performing cyclization in the presence of a strong base, allowing the cyclized compound to react with diphenylphosphoryl chloride to obtain a novel β-lactam compound represented by formula (3), and eliminating the protecting group therefrom. The formulae referred to are diagrammed as follows:

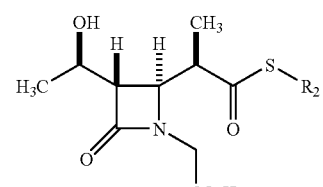

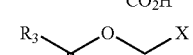

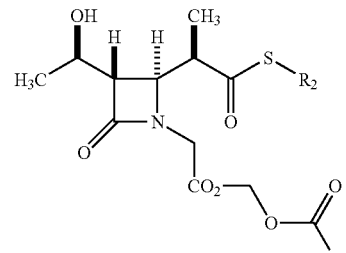

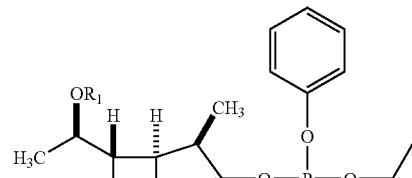

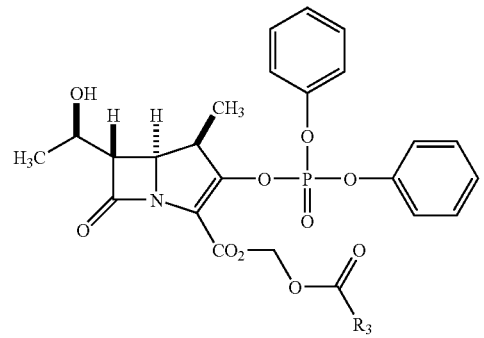

(In the formulae, $R_1$ represents a trimethylsilyl group or a triethylsilyl group; $R_2$ represents an aryl group or a heteroaryl group; $R_2$ represents an aryl group or a heteroaryl group; $R_3$ represents an alkyl group having 1 to 10 carbon atoms or a cycloalkyl group having 3 to 10 carbon atoms; and X represents a halogen atom.)

11 Claims, No Drawings

FOREIGN PATENT DOCUMENTS

| | | |
|---|---|---|
| EP | 0 559 533 A1 | 9/1993 |
| JP | 62-103084 A | 5/1987 |
| WO | WO 2004/035539 A1 | 4/2004 |

OTHER PUBLICATIONS

Greene, Protective Groups in Organic Synthesis (Wiley, 1981), p. 40-41.*

Sakurai, Osamu et al., "A New Synthesis of 1β-Alkylcarbapenems Utilizing Eschenmoser Sulfide Contraction of the Novel Thiazinone Intermediates," *Journal of Organic Chemistry*, 1996, vol. 61, pp. 7889-7894.

International Search Report from Corresponding International Application No. PCT/JP03/14419, dated Mar. 16, 2004, 1 page.

* cited by examiner

INTERMEDIATE FOR CARBAPENEM COMPOUND FOR ORAL ADMINISTRATION AND PROCESS FOR PRODUCING THE SAME

RELATED APPLICATIONS

This application is a nationalization of PCT Application No. PCT/JP2003/014419 filed Nov. 13, 2003. This application claims priority from Japanese Patent Application No. 2002-330127 filed on Nov. 13. 2002.

TECHNICAL FIELD

The present invention relates to a novel β-lactam compound which is extremely useful as a common intermediate for the synthesis of 1β-methylcarbapenem compounds for oral administration and a process for producing the β-lactam compound.

BACKGROUND ART

1β-Methylcarbapenem compounds exhibit excellent antimicrobial activity against a wide range of pathogenic microbes and have excellent stability in vivo. Thus, 1β-methylcarbapenem compounds are one of the antimicrobial agents that are attracting most of the attention. Therefore, recently, energetical research and development has been conducted on drugs for oral administration. A currently commonly used process for producing a 1β-methylcarbapenem compound for oral administration will be described below.

According to a production process described, for example, in Japanese Unexamined Patent Application Publication No. 8-53453 and the Journal of Antibiotics (J. Antibiot.), 429-439, 1997, a compound represented by general formula (7):

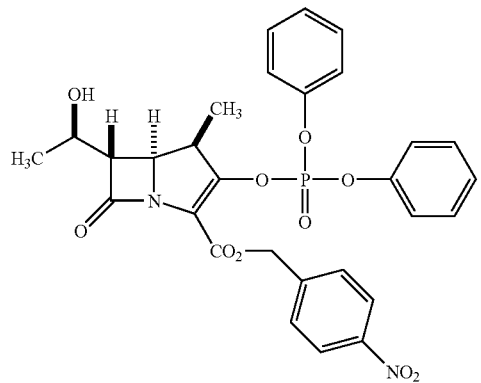

(7)

is allowed to react with any of various thiol compounds (R—SH) to synthesize a compound represented by general formula (8):

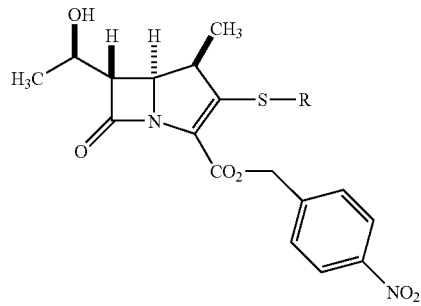

(8)

(wherein R represents a thiol residue); the p-nitrobenzyl group, which is a protecting group, is eliminated, for example, by hydrogenolysis or by reduction using zinc dust to convert the compound (8) into a compound represented by general formula (9):

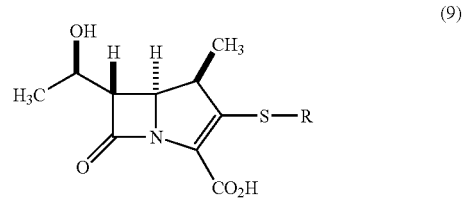

(9)

(wherein R represents a thiol residue); and the carboxylic moiety of the resulting compound (9) is subjected, for example, to pivaloyloxymethylation to produce a compound represented by general formula (10):

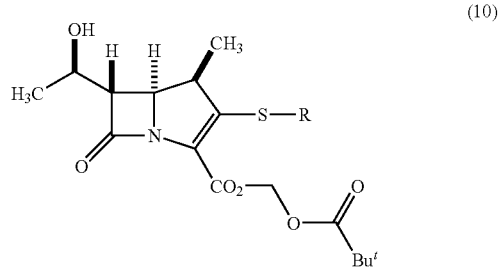

(10)

(wherein R represents a thiol residue, and $Bu^t$ represents a tert-butyl group).

Examples of the compound represented by general formula (10) include a compound represented by general formula (11):

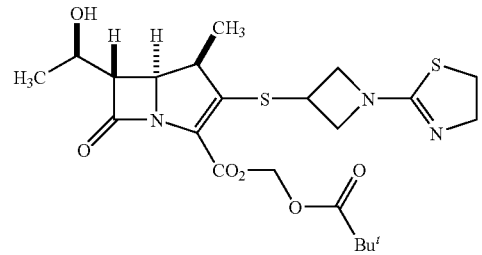

(11)

which is described in the Japanese Unexamined Patent Application Publication No. 8-53453 and Japanese Unexamined Patent Application Publication No. 10-195076; a compound represented by general formula (12):

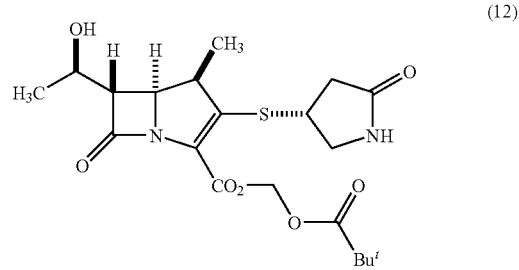

(12)

which is described in the Journal of Antibiotics (J. Antibiot. 429-439, 1997, and Japanese Unexamined Patent Application Publication No. 10-130270; and a compound represented by general formula (13):

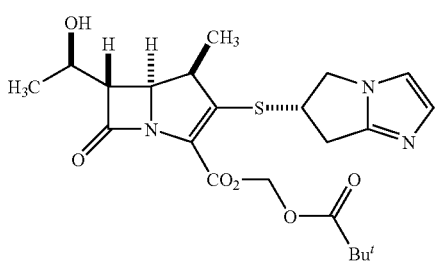

(13)

which is described in Japanese Unexamined Patent Application Publication No. 10-152491. All of these compounds are synthesized by the-process described above.

However, in order to synthesize a 1β-methylcarbapenem compound for oral administration by the process described above, replacement of a protecting group of carboxylic acid is required, and a multistep reaction must be carried out, thus being ineffective. Moreover, a relatively expensive thiol compound, which remains as a thiol residue in the end product, is used at the initial step of synthesis, thus being disadvantageous in terms of production cost and giving rise to a problem.

Furthermore, Japanese Unexamined Patent Application Publication Nos. 8-59663 and 2000-344774 each describe a process in which from a compound represented by general formula (14):

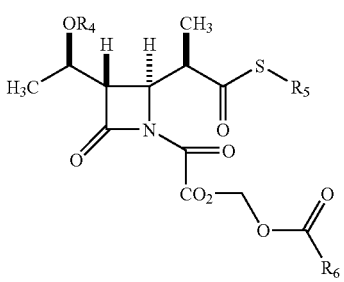

(14)

(wherein $R_4$ represents a protecting group of the hydroxyl group, $R_5$ represents a thiol residue contained in the reaction product 1β-methylcarbapenem compound, and $R_6$ represents an organic group), a compound represented by general formula (15):

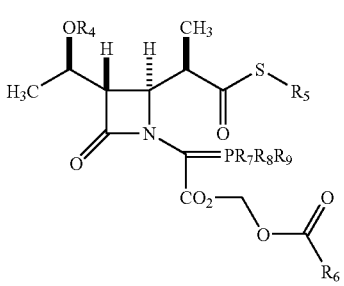

(15)

(wherein $R_4$, $R_5$, and $R_6$ are the same as above; and $R_7$, $R_8$, and $R_9$ each represent a lower alkoxy group having 1 to 4 carbon atoms; or one of $R_7$, $R_8$, and $R_9$ represents an alkyl group having 1 to 4 carbon atoms and the remaining two of $R_7$, $R_8$, and $R_9$ each represent a lower alkoxy group having 1 to 4 carbon atoms) is synthesized, and the compound (15) is cyclized to produce a compound represented by general formula (16):

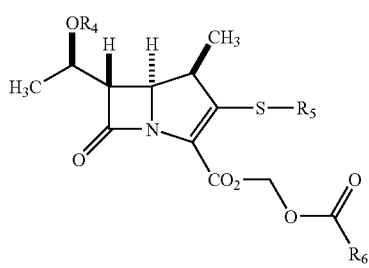

(16)

(wherein $R_4$, $R_5$, and $R_6$ are the same as above)

However, in this production process, as in the process previously described, a relatively expensive thiol compound, which remains as a thiol residue in the end product, is used at the initial step of synthesis, thus being disadvantageous in terms of production cost and giving rise to a problem.

The Journal of Organic Chemistry (J. Org. Chem) 61, 7889-7894, 1996, and Japanese Unexamined Patent Application Publication No. 5-279367 each describe a compound represented by formula (17):

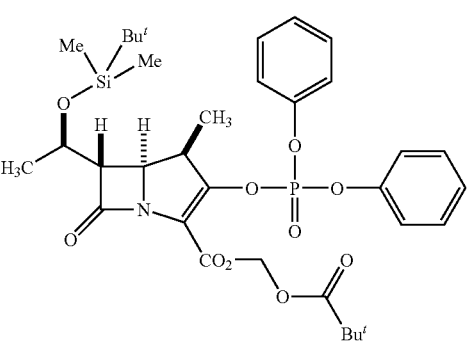

(17)

(wherein Me represents a methyl group, and Bu$^t$ is the same as above). It can be conceived that a 1β-methylcarbapenem compound may be derived from this compound through reaction with any of various thiol compounds and deprotection of the hydroxyl group. However, in the compound (17), since the protecting group of the hydroxyl group is a tert-butyldimethylsilyl group, a reaction reagent that may affect the other functional groups must be used for the deprotection of the hydroxyl moiety, as exemplified in Protective Groups in Organic Synthesis (J. Wiley & Sons, New York), 44-46, 1981. Thus, there is a problem in terms of yield, etc. Although the present inventors have examined various methods for deprotection, it has not been possible to perform the deprotection easily and efficiently.

Under these circumstances, it has been desired to develop a common intermediate capable of producing 1β-methylcarbapenem compounds efficiently and advantageously in terms of production cost.

SUMMARY OF THE INVENTION

The present inventors have conducted energetical research on the development of a novel β-lactam compound and a process for producing the β-lactam compound which allows a thiol compound to be introduced in one step at the final stage in the synthesis of a 1β-methylcarbapenem compound for oral administration, and as a result, the present invention has been achieved.

That is, the present invention provides a process for producing a β-lactam compound including protecting the hydroxyl group of a compound represented by general formula (1):

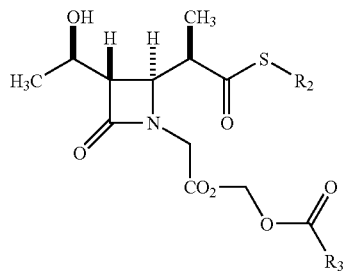

(1)

(wherein $R_2$ represents an aryl group or a heteroaryl group; and $R_3$ represents an alkyl group having 1 to 10 carbon atoms or a cycloalkyl group having 3 to 10 carbon atoms), to produce a compound represented by general formula (2):

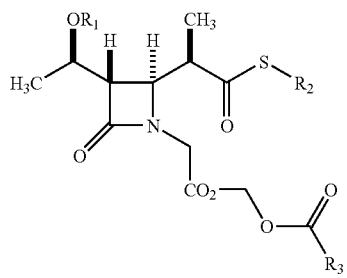

(2)

(wherein $R_1$ represents a trimethylsilyl group or a triethylsilyl group; and $R_2$ and $R_3$ are the same as above); cyclizing the compound (2) in the presence of a strong base; and subsequently allowing the cyclized compound to react with diphenylphosphoryl chloride to produce a compound represented by general formula (3):

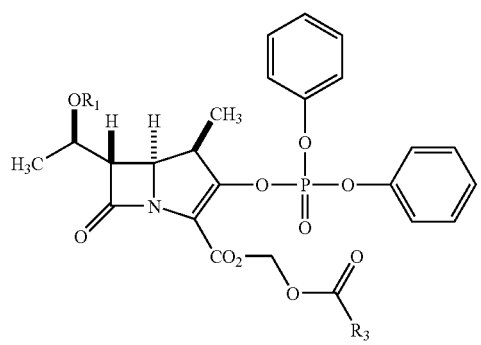

(3)

(wherein $R_1$ and $R_3$ are the same as above).

Furthermore, the present invention provides a process for producing a β-lactam compound represented by general formula (4):

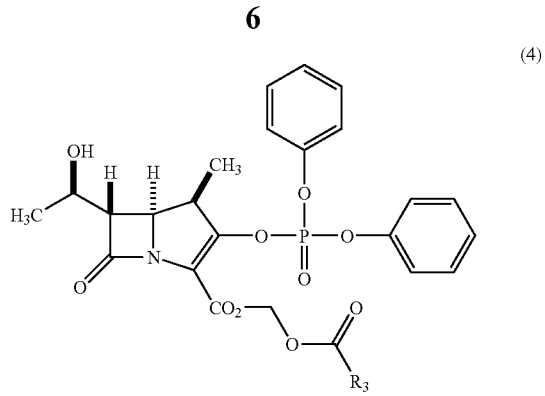

(4)

(wherein $R_3$ is the same as above), the process including deprotecting the hydroxyl moiety of the compound (3) produced by the process described above.

Furthermore, the present invention provides a compound represented by general formula (1):

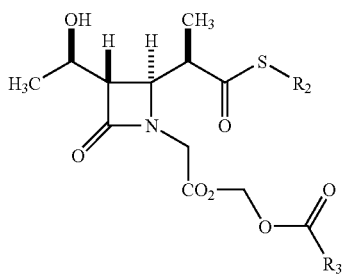

(1)

(wherein $R_2$ and $R_3$ are the same as above).

Furthermore, the present invention provides a compound represented by general formula (3):

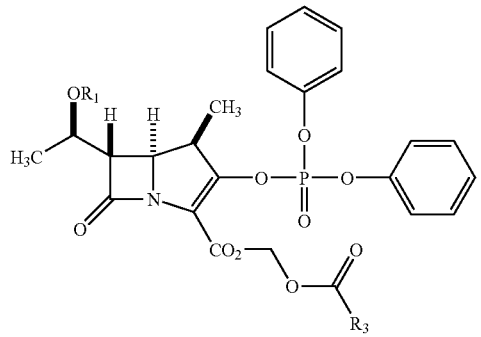

(3)

(wherein $R_1$ and $R_3$ are the same as above).

Furthermore, the present invention provides a compound represented by general formula (4):

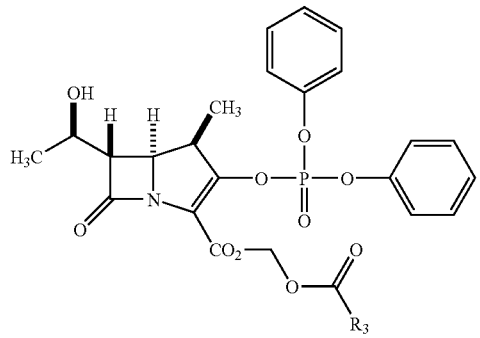

(4)

(wherein $R_3$ is the same as above).

DETAILED DISCLOSURE OF THE INVENTION

The present invention will be described in detail below.

The present invention provides a process for producing a β-lactam compound, the process including protecting the hydroxyl group of a compound represented by general formula (1):

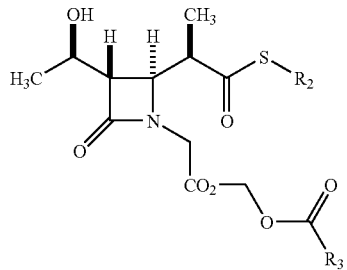
(1)

to produce a compound represented by general formula (2):

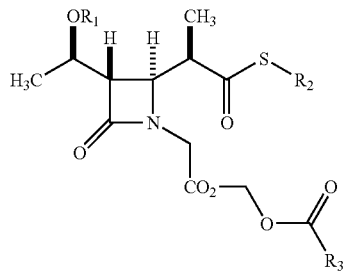
(2)

cyclizing the compound (2) in the presence of a strong base, and subsequently allowing the cyclized compound to react with diphenylphosphoryl chloride to produce a compound represented by general formula (3):

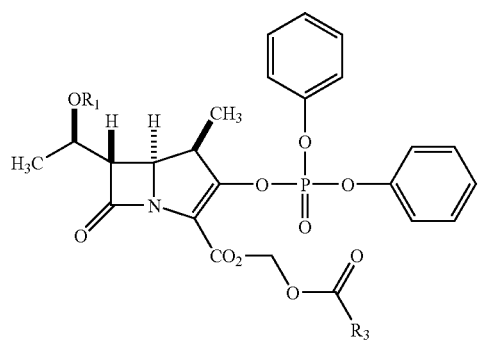
(3)

In the present invention, preferably, the compound represented by general formula (1) is produced by allowing a compound represented by general formula (5):

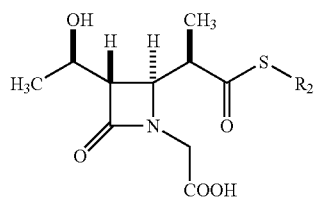
(5)

to react with a compound represented by general formula (6):

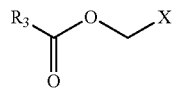
(6)

in the presence of a base.

In the present invention, the compound represented by general formula (3) produced by the process for producing the β-lactam compound may be converted into a β-lactam compound represented by general formula (4):

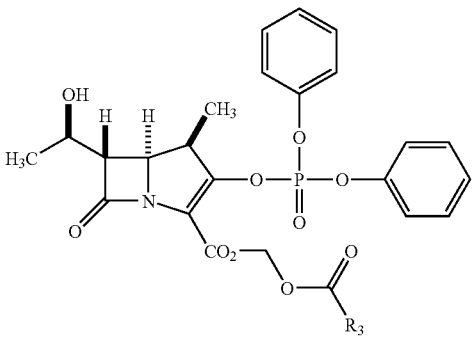
(4)

through deprotection of the hydroxyl moiety.

First, the substituents in the compounds will be described. In formulae (2) and (3), the protecting group $R_1$ of the hydroxyl group is a trimethylsilyl group or a triethylsilyl group, and particularly preferably a trimethylsilyl group. The present inventors have found, through energetical research, that these substituents can be eliminated under mild reaction conditions with minimum decomposition of the other functional group moieties during deprotection reaction of the protecting group $R_1$ of the compound (3) used in the production process of the present invention.

In formulae (1), (2), and (5), $R_2$, which is a thiol residue, represents an aryl group or a heteroaryl group that may be substituted with a halogen atom, such as chlorine, bromine, or iodine, a nitro group, an alkyl group having 1 to 3 carbon atoms, or an alkoxy group having 1 to 3 carbon atoms.

Examples of the aryl group include a phenyl group, a halogenophenyl group substituted with one to three halogen atoms, such as chlorine, bromine, or iodine, a p-nitrophenyl group, an o-nitrophenyl group, a p-methoxyphenyl group, a 1-naphthyl group, and a 2-naphthyl group.

Examples of the heteroaryl group include a 2-pyridyl group, a 3-pyridyl group, a 4-pyridyl group, a 2-pyrimidyl group, a 2-(4,6-dimethyl)pyrimidyl group, a 2-benzothiazolyl group, a 2-benzimidazolyl group, a 2-benzoxazolyl group, and a 2-thienyl group.

As $R_2$, an aryl group is preferable, and a phenyl group and a halogenophenyl group are more preferable in view of ease of availability, economics, reactivity, etc. As the halogenophenyl group, a p-chlorophenyl group is preferable.

In formulae (1), (2), (3), (4), and (6), the substituent $R_3$, which is ultimately contained in the alkanoyloxymethyl moiety of the carboxylate residue in a compound that can be developed as a 1β-methylcarbapenem compound for oral administration, represents an alkyl group having 1 to 10 carbon atoms or a cycloalkyl group having 3 to 10 carbon atoms.

Examples of the alkyl group having 1 to 10 carbon atoms include a methyl group, an ethyl group, a n-propyl, an isopropyl group, a n-butyl group, an isobutyl group, a sec-butyl group, a tert-butyl group, a n-octyl group, and a n-decanyl group.

The cycloalkyl group having 3 to 10 carbon atoms may have a substituent, and as the substituent, an alkyl group having 1 to 4 carbon atoms, such as a methyl group or an ethyl group, may be mentioned. Examples of the cycloalkyl group having 3 to 10 carbon atoms include a cyclopropyl group, a cyclohexyl group, a 1-methylcyclohexyl group, and a 4-methylcyclohexyl group.

As the substituent $R_3$, a tert-butyl group, which is often used in the development of carbapenem compounds for oral administration, is particularly preferable.

In formula (6), the substituent X represents a halogen atom, such as a fluorine atom, a chlorine atom, a bromine atom, or an iodine atom. In view of ease of availability, reactivity, stability, etc. of the compound (6), a chlorine atom is particularly preferable.

Production processes of the present invention will now be described below.

The compound represented by general formula (5), which is preferably used as a starting material in the present invention, can be easily produced, for example, by a process described in the Chemical and Pharmaceutical Bulletin (Chem. Pharm. Bull.), 42, 1381-1387, 1994. This compound can be easily synthesized in the form of a desired optically active substance as a material for synthesis of a 1β-methylcarbapenem compound.

By allowing the compound (5) to react with an alkanoyloxymethyl halide represented by formula (6) in the presence of a base, a β-lactam compound represented by formula (1) can be derived.

The reaction is carried out using an inert solvent that does not decompose the compound (5) and the compound (6). The inert solvent is not particularly limited. Examples thereof include ether solvents, such as tetrahydrofuran, dioxane, and diethyl ether; aromatic hydrocarbon solvents, such as benzene, toluene, and xylene; amide solvents, such as N,N-dimethylformamide and N,N-dimethylacetamide; dimethyl sulfoxide, acetonitrile, acetone, methylene chloride, and mixed solvents of these. From the standpoint of reaction rate, N,N-dimethylformamide and N,N-dimethylacetamide are particularly preferable.

The amount of the alkanoyloxymethyl halide (6) used for the reaction must be 1.0 or more molar times and is preferably 1.1 to 3.0 molar times the amount of the compound (5).

Furthermore, as the base, any base that is generally used in the reaction for forming an ester using a carboxylic acid and an alkyl halide can be used. Examples thereof include organic amines and alkali metal salts.

Examples of the organic amines include triethylamine, diisopropylethylamine, dicyclohexylamine, 1,8-diazabicyclo[5.4.0]undec-7-ene (DBU), and morpholine. The amount of use thereof must be 1.0 or more molar times and is preferably 1.1 to 2.0 molar times the amount of the compound (5).

Furthermore, examples of the alkali metal salts include alkali metal carbonates, such as sodium carbonate, potassium carbonate, and cesium carbonate; and alkali metal bicarbonates, such as sodium bicarbonate and potassium bicarbonate. When an alkali metal carbonate is used, the amount of use thereof must be 0.5 or more molar times and is preferably 1.1 to 2.0 molar times the amount of the compound (5). When an alkali metal bicarbonate is used, the amount of use thereof must be 1.0 or more molar times and is preferably 1.1 to 2.0 molar times the amount of the compound (5).

Furthermore, an additive, as a reaction promoter, may be added to the reaction described above if necessary.

Examples of the additive include alkali metal halides, such as sodium iodide and lithium bromide; and quaternary ammonium halides, such as tetrabutylammonium bromide and benzyltriethylammonium chloride. The amount of use thereof is preferably 1.0 or more molar times and most preferably 1.0 to 1.5 molar times the amount of the compound (6).

The reaction described above is usually carried out at 0° C. to 80° C. From the standpoint of inhibiting decomposition of the reactants and product, the reaction is preferably carried out at 10° C. to 40° C.

Furthermore, the reaction time is usually 1 to 50 hours and preferably 2 to 30 hours from the same standpoint.

Of course, the progress of reaction can be determined by analytical means, such as thin-layer chromatography (TLC) or high-performance liquid chromatography (HPLC).

The target compound (1) can be isolated from the reaction mixture by means of pH adjustment, extraction, liquids separation, washing, concentration, purification, and others, which are often commonly performed in organic reactions.

Additionally, the compound (1) obtained by the reaction described above is a novel compound, of which application as a useful precursor for producing a common intermediate for the synthesis of 1β-methylcarbapenem compounds for oral administration has been confirmed by the present inventors.

The compound (1) obtained by the reaction described above is subsequently converted into the compound (2) by the protection of the hydroxyl group.

This is a reaction in which a silyl protecting group is introduced into the hydroxyl group, and general conditions for introducing the silyl protecting group, for example, those described in Protective Groups in Organic Synthesis (J. Wiley & Sons, New York), 39-50, 1981, may be employed. In the present invention, a trimethylsilyl group or a triethylsilyl group is introduced. The compound (2) can be derived by allowing the compound (1) to react with chlorotrimethylsilane or chlorotriethylsilane in an inert solvent in the presence of a base, such as an amine. This method is most commonly used and is most suitable for the production of the compound (2).

The amount of chlorotrimethylsilane or chlordtriethylsilane used in this stage must be 1.0 or more molar times and is preferably 1.1 to 3.0 molar times the amount of the compound (1).

Furthermore, examples of the amine used as the base include triethylamine, diisopropylethylamine, pyridine, and imidazole. The amount of use thereof must be 1.0 or more molar times and is preferably 1.1 to 3.0 molar times the amount of the compound (1).

As the inert solvent, any solvent that is inert so as not to decompose the chlorotrialkylsilane described above may be used without limitation. Examples thereof include ether solvents, such as tetrahydrofuran, dioxane, and diethyl ether; aromatic hydrocarbon solvents, such as benzene, toluene, and xylene; amide solvents, such as N,N-dimethylformamide and N,N-dimethylacetamide; dimethyl sulfoxide, acetonitrile, acetone, methylene chloride, and mixed solvents of these.

The reaction described above is usually carried out at 0° C. to 100° C. From the standpoint of inhibiting decomposition of the reactants and product, the reaction is preferably carried out at 10° C. to 60° C.

Furthermore, the reaction time is usually 0.5 to 50 hours and preferably 1 to 30 hours from the same standpoint.

Additionally, as described above, the progress of reaction can be followed by analytical means.

The compound (2) can be isolated from the reaction mixture by means of pH adjustment, extraction, liquids separation, washing, concentration, purification, and others, which are often commonly performed in organic reactions. During this stage, if the compound (2) is subjected to acidic conditions, the protecting group on the hydroxyl group is eliminated and the compound (2) reverts back to the starting compound (1). Therefore, sufficient care must be taken not to cause acidic conditions.

The compound (2) obtained by the reaction described above is converted into the compound (3) by cyclization in the presence of a strong base and subsequent treatment with diphenylphosphoryl chloride.

Examples of the strong base which may be preferably used in the cyclization reaction of the compound (2) include alkali metal alkoxides, such as potassium tert-butoxide and sodium tert-butoxide; alkali metal amides, such as lithium bis(trimethylsilyl)amide, sodium bis(trimethylsilyl)amide, and potassium bis(trimethylsilyl)amide; and alkali metal hydrides, such as sodium hydride and potassium hydride. In this reaction, since the thioester group and the alkanoyloxymethyl group are present in the compound (2), a base that minimizes the decomposition of these functional groups is desired, and potassium tert-butoxide, sodium bis(trimethylsilyl)amide, and sodium hydride are particularly preferable.

Furthermore, the strong base is used desirably in an amount that allows the cyclization reaction to proceed sufficiently. Preferably, the amount of use is 2 to 3 molar times the amount of the compound (2).

In the cyclization reaction, as cyclization progresses, formation of a metal thiolate as a by-product occurs. In order to convert the metal thiolate into a compound in a form that does not adversely affect the subsequent reaction, a scavenger is preferably used.

Examples of the scavenger which may be used include alkylating agents, such as methyl iodide, propyl iodide, allyl bromide, benzyl bromide, and methyl p-toluenesulphonate; sulfonylating agents, such as p-toluenesulfonyl chloride and methanesulfonyl chloride; and phosphorylating agents, such as diphenylphosphoryl chloride. The scavenger is used desirably in an amount equal to the amount of the metal thiolate formed from the compound (2) as a by-product. Preferably, the amount of use is 1.0 to 1.5 molar times the amount of the compound (2).

Subsequently, the compound (3) is produced by reaction between the reaction intermediate obtained by cyclizing the compound (2) and diphenylphosphoryl chloride. This reaction is usually carried out in the same reactor vessel as that used for the cyclization reaction.

Diphenylphosphoryl chloride must be used in an amount that allows the reaction to proceed sufficiently. The amount of use is preferably 1.0 to 1.5 molar times the amount of the compound (2). Since diphenylphosphoryl chloride can also act as a scavenger as described above, in such a case, diphenylphosphoryl chloride is used in an amount of 2 or more molar times the amount of the compound (2) so that the metal thiolate is trapped and so as to also serve as a phosphorylating agent.

The cyclization and phosphorylation reactions described above are carried out in an inert solvent. The inert solvent is not particularly limited. Preferred examples thereof include ether solvents, such as tetrahydrofuran, dioxane, and diethyl ether; aromatic hydrocarbon solvents, such as benzene, toluene, and xylene; amide solvents, such as N,N-dimethylformamide and N,N-dimethylacetamide; dimethyl sulfoxide, acetonitrile, acetone, methylene chloride, and mixed solvents of these. From the standpoints of solubilities of the base and the compound (2), tetrahydrofuran or a mixed solvent of tetrahydrofuran and toluene are most preferable. The mixing ratio is not particularly limited as long as the reaction reagent is dissolved.

The cyclization and phosphorylation reactions described above are usually carried out at −78° C. to 60° C. From the standpoint of inhibiting decomposition of the reactants and product, the reactions are preferably carried out at −78° C. to 10° C.

Furthermore, the cyclization reaction time is usually 1 minute to 20 hours, and preferably 5 minutes to 5 hours.

Furthermore, the phosphorylation reaction time is usually 5 minutes to 30 hours, and preferably 30 minutes to 10 hours.

Additionally, as described above, the progress of reactions can be followed by analytical means.

The compound (3) can be isolated from the reaction mixture by means of pH adjustment, extraction, liquids separation, washing, concentration, purification, and others, which are often commonly performed in organic reactions.

Additionally, the compound (3) obtained by the reactions described above is a novel compound, of which application as a useful precursor for producing a common intermediate for the synthesis of 1β-methylcarbapenem compounds for oral administration has been confirmed by the present inventors.

Subsequently, the compound (4) can be derived from the compound (3) by eliminating $R_1$, i.e., the protecting group of the hydroxyl group.

As the method for deprotection, general deprotection conditions for eliminating the silyl protecting group, for example, those described in Protective Groups in Organic Synthesis (J. Wiley & Sons, New York), 39-50, 1981, may be employed.

In order to eliminate the protecting group under mild reaction conditions with minimum decomposition of the other functional group moieties in the compound during the deprotection reaction, a method is preferably used in which the pH of the reaction mixture after the cyclization and phosphorylation of the compound (2) is adjusted so as to achieve acidic conditions, and thus the hydroxyl moiety is deprotected. However, the compound (4) may be derived from the compound (3) after the compound (3) has been recovered.

The acidic conditions used in this stage are not particularly limited as long as the pH is 7 or less. Preferably, the pH is 2 to 6. Thereby, the silyl protecting group can be extremely easily eliminated. Furthermore, in order to create the acidic conditions, for example, phosphoric acid, aqueous citric acid, hydrochloric acid, or the like may be added to the mixture.

The compound (4) is a novel compound, and as will be described below, useful application of the compound (4) as a common intermediate for the synthesis of 1β-methylcarbapenem compounds for oral administration has been confirmed by the present inventors for the first time.

By allowing the compound (4) thus obtained to react with a thiol compound (R'—SH) in the presence of a base, any of 1β-methylcarbapenem compounds represented by general formula (20):

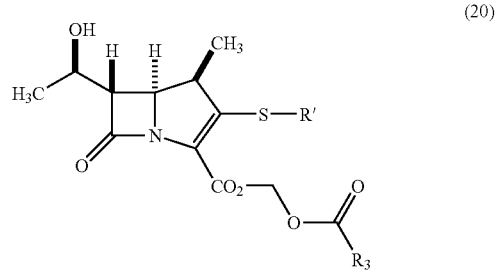

(20)

(wherein R' represents a thiol residue; and $R_3$ is the same as above) can be derived by one step.

Furthermore, by allowing the compound (3) before the deprotection to react with a thiol compound in the presence with a base, a 1β-methylcarbapenem compound represented by general formula (21):

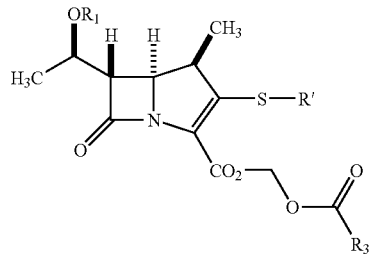

(wherein R', R₁, and R₃ are the same as above) is obtained, and then by deprotecting the hydroxyl moiety, any of 1β-methylcarbapenem compounds for oral administration may be derived. Without isolating the compound (3) or (4), a desired 1β-methylcarbapenem compound can be derived directly.

In such a case, first, as described above, the compound (2) is cyclized and then a phosphorylation reaction with diphenylphosphoryl chloride is carried out to produce the compound (3). Subsequently, the compound (3) is allowed to react with a thiol compound (R'—SH) in the presence of a base.

Here, the base used in the reaction with the thiol compound may be the same as or different from the strong base used in the cyclization reaction described above.

As the base other than the strong base used in the cyclization of the compound (2) described above, an organic amine or an alkali metal salt can be used. Examples of the organic amine include triethylamine, diisopropylethylamine, 4-dimethylaminopyridine, 1,8-diazabicyclo[5.4.0]-undec-7-ene (DBU), 1,5-diazabicyclo[4.3.0]-non-5-ene (DBN), and 1,4-diazabicyclo[2.2.2]octane (DABCO). Examples of the alkali metal salt include alkali metal carbonates, such as sodium carbonate, potassium carbonate, and cesium carbonate; and alkali metal bicarbonates, such as sodium bicarbonate and potassium bicarbonate.

Furthermore, the reaction may be accelerated by the addition of a different inert solvent from the one used in the cyclization reaction.

Preferred examples of the inert solvent which is further added to accelerate the reaction include acetonitrile, N,N-dimethylformamide, and N,N-dimethylacetamide.

The 1β-methylcarbapenem compound produced as described above can be converted into a desired 1β-methylcarbapenem compound for oral administration by the above-described common method in which deprotection of the hydroxyl group is performed, and preferably by a deprotection method in which the conditions are set to be the same as those described above to minimize the decomposition of the other functional group moieties.

BEST MODE FOR CARRYING OUT THE INVENTION

While the present invention will be described in more detail based on the examples and reference examples below, it is to be understood that the invention is not limited thereto. Abbreviations and their meanings used in the examples and reference examples will be described below.

Me: methyl group
Bu$^t$: tert-butyl group
TMS: trimethylsilyl group
TES: triethylsilyl group

EXAMPLE 1

Production of (3S,4S)-4-[(1R)-1-(p-chlorophenylthiocarbonyl)ethyl]-3-[(1R)-1-hydroxyethyl]-1-pivaloyloxymethyloxycarbonylmethyl-2-azetidinone

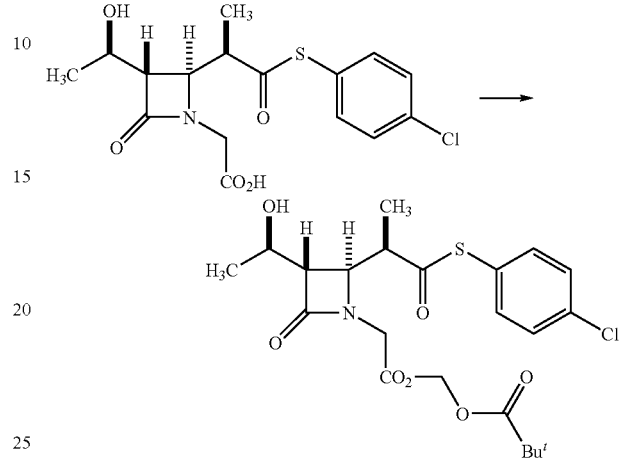

At room temperature (25° C.) 8.18 g (22.0 mmol) of (3S,4S)-1-carboxymethyl-4-[(1R)-1-(p-chlorophenylthiocarbonyl)ethyl]-3-[(1R)-1-hydroxyethyl]-2-azetidinone was dissolved in 18 ml of dimethylformamide, and 5.5 ml (40.0 mmol) of pivaloyloxymethyl chloride and 5.75 g (40.3 mmol) of sodium iodide were sequentially added thereto. Subsequently, 4.2 ml (25.3 mmol) of diisopropylethylamine was added dropwise thereto, and stirring was performed at the same temperature for 20 hours. The reaction solution was diluted with 120 ml of toluene, and washing was performed several times using 2.5% aqueous sodium bicarbonate and water. The resulting toluene solution was dried over sodium sulfate, and then the solvent was removed by distillation. The resulting oily residue was dissolved in 60 ml of toluene at room temperature, and 120 ml of hexane was added to the toluene solution to precipitate crystals. The resulting crystals were separated by filtration and washed. Thereby, 9.46 g of white crystals of the target compound was produced (yield 92.7%).

NMR δ (CDCl₃): 1.19 (9H, s), 1.32-1.34 (6H, m), 3.11-3.18 (2H, m), 3.87 (1H, d, J=18.1 Hz), 4.15 (1H, dd, J=2.4, 4.4 Hz), 4.22-4.24 (1H, m), 4.35 (114, d, J=18.1 Hz), 5.76 (2H, s), 7.31 (2H, d, J=8.8 Hz), 7.40 (2H, d, J=8.8 Hz)

EXAMPLE 2

Production of (3S,4S)-4-[(1R)-1-(phenylthiocarbonyl)ethyl]-3-[(1R)-1-hydroxyethyl]-1-pivaloyloxymethyloxycarbonylmethyl-2-azetidinone

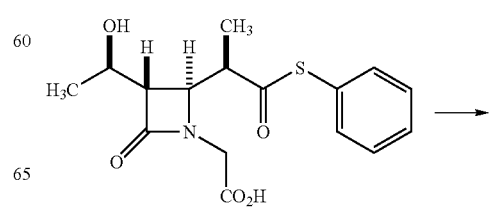

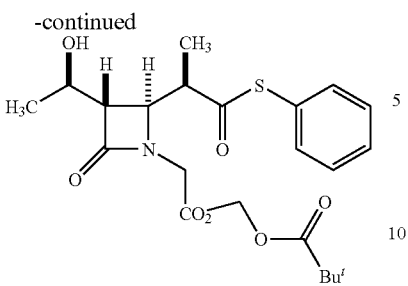

At room temperature (25° C.), 1.35 g (4.0 mmol) of (3S, 4S)-1-carboxymethyl-4-[(1R)-1-(phenylthiocarbonyl) ethyl]-3-[(1R)-1-hydroxyethyl]-2-azetidinone was dissolved in 8 ml of dimethylformamide, and 1.20 (8.0 mmol) of-pivaloyloxymethyl chloride and 1.20 g (8.0 mmol) of sodium iodide were sequentially added thereto. Subsequently, 0.68 g (5.3 mmol) of diisopropylethylamine was added dropwise thereto, and stirring was performed at the same temperature for 6 hours. The reaction solution was diluted with 40 ml of ethyl acetate, and washing was performed several times using 5% aqueous sodium bicarbonate and water. The resulting ethyl acetate solution was dried over sodium sulfate, and then the solvent was removed by distillation. Thereby, 1.88 g of the target compound was produced.

NMR δ (CDCl$_3$): 1.19 (9H, s), 1.32-1.34 (6H, m), 3.12-3.19 (2H, m), 3.89 (1H, d, J=18.3 Hz), 4.15 (1H, dd, J=2.2, 4.1 Hz), 4.19-4.27 (1H, m), 4.35 (1H, d, J=18.3 Hz), 5.76 (2H, s), 7.36-7.43 (5H, m)

EXAMPLE 3

Production of (4R, 5R, 6S)-6-[(1R)-1-trimethylsilyloxyethyl]-3-diphenylphosphoryloxy-4-methyl-7-oxo-1-azabicyclo[3.2.0]hept-2-ene-2-carboxylic acid pivaloyloxymethyl ester

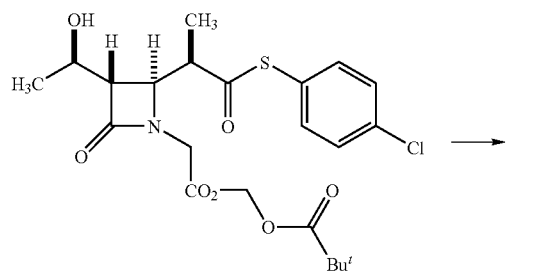

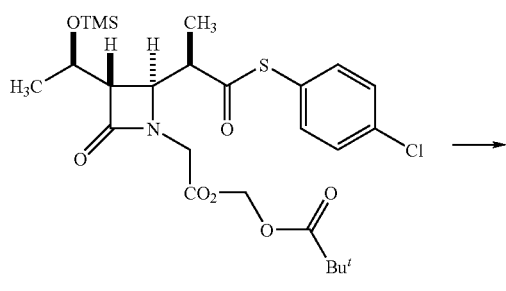

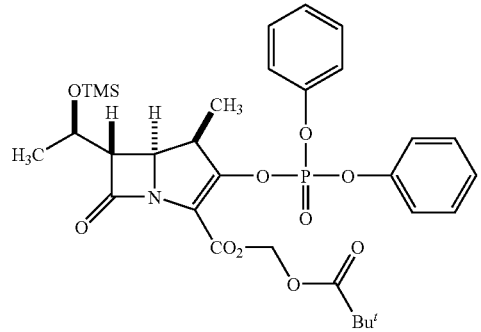

A solution was prepared by dissolving 0.49 g (1.0 mmol) of (3S, 4S)-4-[(1R)-1-(p-chlorophenylthiocarbonyl)ethyl]-3-[(1R)-1-hydroxyethyl]-1-pivaloyloxymethyloxycarbonyl-methyl-2-azetidinone synthesized as in Example 1 in 5 ml of toluene, and 0.17 g (1.7 mmol) of triethylamine was added thereto at room temperature. Subsequently, 0.17 g (1.5 mmol) of chlorotrimethylsilane was added dropwise thereto, and stirring was performed at the same temperature for 14 hours. The reaction solution was diluted with 5 ml of toluene, and washing was performed several times with water. The resulting toluene solution was dried over sodium sulfate, and then the solvent was removed by distillation.

The resulting oily residue was dissolved in 8 ml of tetrahydrofuran, and cooling was performed to −25° C. After 0.089 g (2.1 mmol) of sodium hydride was added to the resulting solution, stirring was performed for 135 minutes. At the same temperature, 0.18 g (1.05 mmol) of benzyl bromide was added to the mixture, followed by stirring for 15 minutes, and then 0.30 g (1.1 mmol) of diphenylphosphoryl chloride was added thereto, followed by stirring for 2.5 hours. The reaction solution was diluted with 50 ml of toluene, and washing was performed several times using 2.5% aqueous sodium bicarbonate and water under ice cooling. The resulting toluene solution was dried over sodium sulfate, and then the solvent was removed by distillation. The target compound was thereby produced.

As the means for following the progress of reaction, analysis was carried out by high-performance liquid chromatography. The reaction solution and the resulting target compound were dissolved in an eluent prepared by mixing acetonitrile, water, and phosphoric acid at a ratio of 700/300/1 and analysis was carried out. As a result, detection was made at the same retention time as that for the product produced in Example 5, which will be described below. It was thus confirmed that the trimethylsilyl group, i.e., the protecting group of the hydroxyl group, was easily eliminated.

NMR δ (CDCl$_3$): 0.11 (9H, s), 1.19-1.29 (15H, m), 3.24 (1H, dd, J=2.9, 6.6 Hz), 3.45-3.50 (1H, m), 4.07-4.19 (2H, m), 5.78 (1H, d, J=5.5 Hz), 5.81 (1H, d, J=5.5 Hz), 7.15-7.40 (12H, m)

EXAMPLE 4

Production of (4R, 5R, 6S)-6-[(1R)-1-trimethylsilyloxyethyl]-3-diphenylphosphoryloxy-4-methyl-7-oxo-1-azabicyclo[3.2.0]hept-2-ene-2-carboxylic acid pivaloyloxymethyl ester

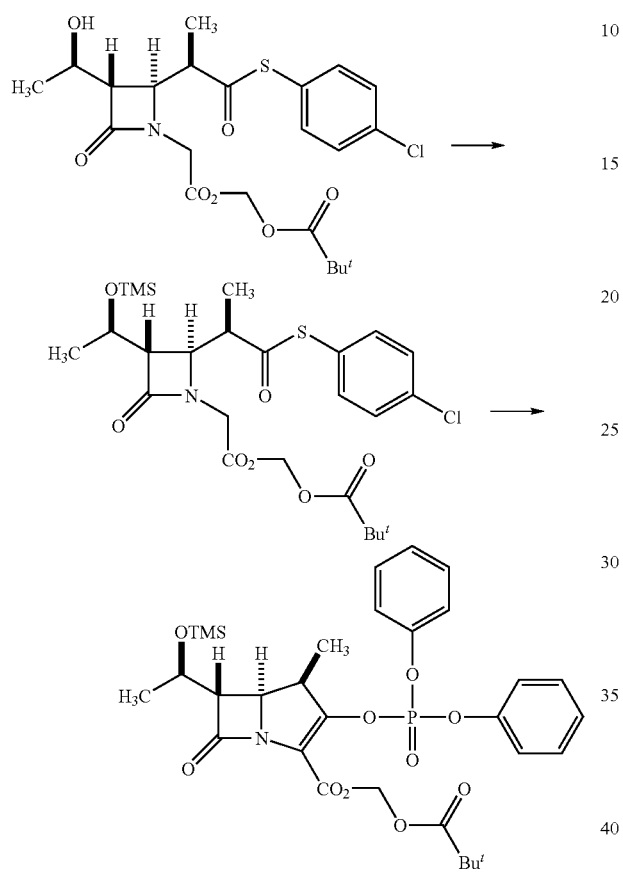

A solution was prepared by dissolving 1.997 g (4.1 mmol) of (3S, 4S)-4-[(1R)-1-(p-chlorophenylthiocarbonyl)ethyl]-3-[(1R)-1-hydroxyethyl]-1-pivaloyloxymethyloxycarbonylmethyl-2-azetidinone synthesized as in Example 1 in 20 ml of toluene, and 0.88 mL (6.4 mmol) of triethylamine was added thereto at room temperature. Subsequently, 0.78 mL (6.2 mmol) of chlorotrimethylsilane was added dropwise thereto, and stirring was performed at the same temperature for 15 hours. The reaction solution was diluted with 5 ml of toluene, and washing was performed several times with water. The resulting toluene solution was dried over sodium sulfate, and then the solvent was removed by distillation.

The resulting oily residue (2.63 g) was dissolved in 22.5 ml of tetrahydrofuran, and cooling was performed to −70° C. After 0.956 g (8.5 mmol) of potassium tert-butoxide was added to the resulting solution, stirring was performed for 15 minutes. At the same temperature, 0.26 mL (4.2 mmol) of methyl iodide was added to the mixture, and stirring was performed for 2.5 minutes while the temperature was gradually increased to −35° C. Subsequently, at −35° C., 1.0 mL (4.9 mmol) of diphenylphosphoryl chloride was added to the mixture, and stirring was performed for 1.8 hours while the temperature was gradually increased to −9° C. The reaction solution was diluted with 20 ml of toluene, and washing was performed several times using 2.5% aqueous sodium bicarbonate and water under ice cooling. The resulting toluene solution was dried over sodium sulfate, and then the solvent was removed by distillation. The target compound was thereby produced.

EXAMPLE 5

Production of (4R, 5R, 6S)-6-[(1R)-1-hydroxyethyl]-3-diphenylphosphoryloxy-4-methyl-7-oxo-1-azabicyclo[3.2.0]hept-2-ene-2-carboxylic acid pivaloyloxymethyl ester

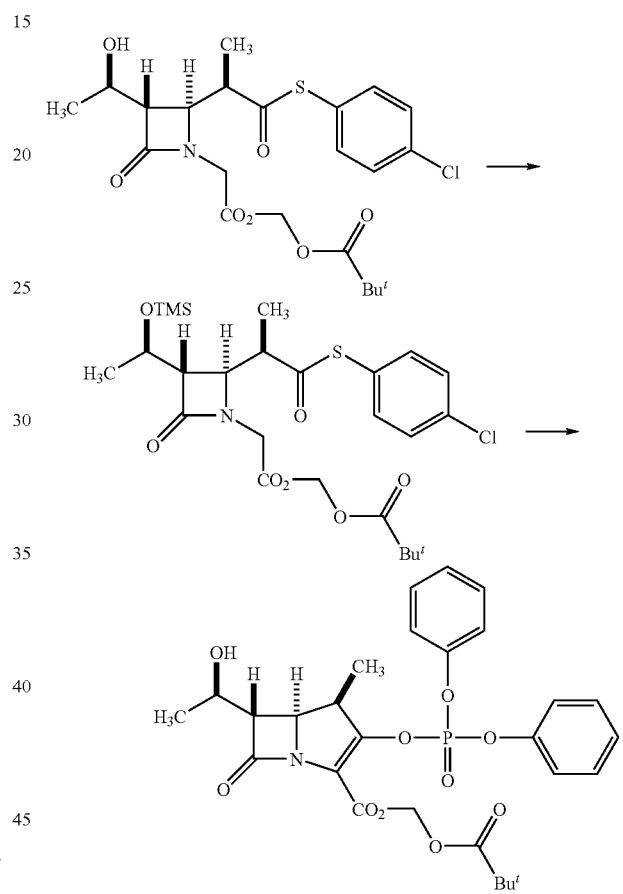

A solution was prepared by dissolving 0.97 g (2.0 mmol) of (3S, 4S)-4-[(1R)-1-(p-chlorophenylthiocarbonyl)ethyl]-3-[(1R)-1-hydroxyethyl]-1-pivaloyloxymethyloxycarbonylmethyl-2-azetidinone synthesized as in Example 1 in 5 ml of toluene, and 0.50 g (5.0 mmol) of triethylamine was added thereto at room temperature. Subsequently, 0.39 g (3.6 mmol) of chlorotrimethylsilane was added dropwise thereto, and stirring was performed at the same temperature for 15 hours. The reaction solution was diluted with toluene, and washing was performed several times with water. The resulting toluene solution was dried over sodium sulfate, and then the solvent was removed by distillation.

The resulting oily residue was dissolved in 15 ml of a mixed solvent including tetrahydrofuran and toluene at a volume ratio of 1:2, and cooling was performed to −25° C. After 0.475 g (4.2 mmol) of potassium tert-butoxide was added to the resulting solution, stirring was performed for 1 hour. At the same temperature, 0.30 g (2.1 mmol) of methyl iodide was added to the mixture, followed by stirring for 20 minutes, and then 0.60 g (2.2 mmol) of diphenylphosphoryl chloride was added thereto, followed by stirring for 2.5 hours.

Ethyl acetate and water were added to the reaction solution under ice cooling. The pH of the mixed solution was adjusted to 3 with 1 N aqueous hydrochloric acid. The separated ethyl acetate solution was washed several times with aqueous sodium bicarbonate and water and then dried over sodium sulfate. The solvent was removed by distillation. The target compound was thereby produced.

NMR δ (CDCl$_3$): 1.18-1.20 (12H, m), 1.29 (3H, d, J=4.9 Hz), 3.28 (1H, dd, J=2.4, 6.3 Hz), 3.45-3.51 (1H, m), 4.17-4.21 (2H, m), 5.77 (1H, d, J=5.5 Hz), 5.81 (1H, d, J=5.5 Hz), 7.21-7.40 (12H, m)

EXAMPLE 6

Production of (4R, 5R, 6S)-6-[(1R)-1-triethylsilyloxyethyl]-3-diphenylphosphoryloxy-4-methyl-7-oxo-1-azabicyclo[3.2.0]hept-2-ene-2-carboxylic acid pivaloyloxymethyl ester

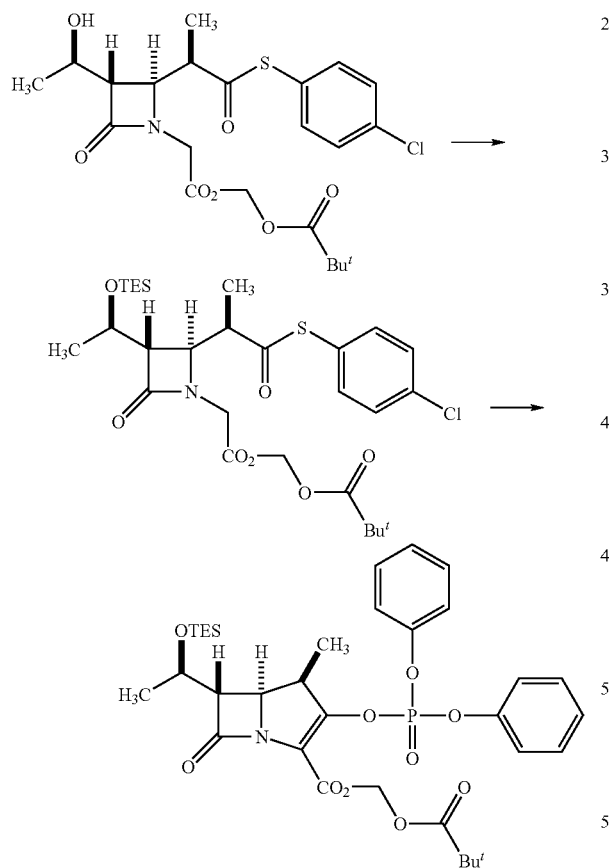

A solution was prepared by dissolving 0.493 g (1.0 mmol) of (3S, 4S)-4-[(1R)-1-(p-chlorophenylthiocarbonyl)ethyl]-3-[(1R)-1-hydroxyethyl]-1-pivaloyloxymethyloxycarbonyl-methyl-2-azetidinone synthesized as in Example 1 in 10 ml of toluene, and 0.17 g (1.7 mmol) of triethylamine was added thereto at room temperature. Subsequently, 0.24 g (1.6 mmol) of chlorotriethylsilane was added dropwise thereto, and stirring was performed at the same temperature for 22 hours. The reaction solution was diluted with 10 ml of toluene, and washing was performed several times with water. The resulting toluene solution was dried over sodium sulfate, and then the solvent was removed by distillation.

The resulting oily residue was dissolved in 6 ml of tetrahydrofuran, and cooling was performed to −25° C. After 0.232 g (2.1 mmol) of potassium tert-butoxide was added to the resulting solution, stirring was performed for 60 minutes. At the same temperature, 0.19 g (1.05 mmol) of benzyl bromide was added to the mixture, followed by stirring for 20 minutes, and then 0.30 g (1.1 mmol) of diphenylphosphoryl chloride was added thereto, followed by stirring for 2 hours. The reaction solution was diluted with 50 ml of toluene, and washing was performed several times using 2.5% aqueous sodium bicarbonate and water under ice cooling. The resulting toluene solution was dried over sodium sulfate, and then the solvent was removed by distillation. The target compound was thereby produced.

NMR δ (CDCl$_3$): 0.59-0.62 (6H, m), 0.94 (9H, t, J=8.1 Hz), 1.19-1.28 (15H, m), 3.23 (1H, dd, J=2.9, 6.6 Hz), 3.42-3.46 (1H, m), 4.13 (1H, dd, J=2.9, 10.3 Hz), 4.18-4.23 (1H, m), 5.78 (1H, d, J=5.5 Hz), 5.81 (1H, d, J=5.5 Hz), 7.15-7.43 (12H, m)

EXAMPLE 7

Production of (4R, 5R, 6S)-6-[(1R)-1-trimethylsilyloxyethyl]-3-diphenylphosphoryloxy-4-methyl-7-oxo-1-azabicyclo[3.2.0]hept-2-ene-2-carboxylic acid pivaloyloxymethyl ester

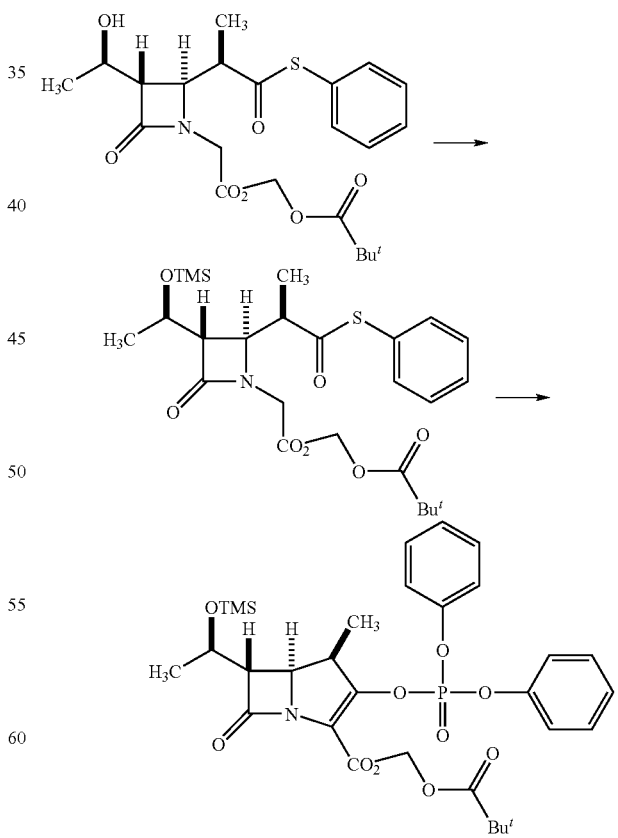

A solution was prepared by dissolving 0.94 g of an oily residue containing (3S,4S)-4-[(1R)-1-(phenylthiocarbonyl)

ethyl]-3-[(1R)-1-hydroxyethyl]-1-pivaloyloxymethyloxy-carbonylmethyl-2-azetidinone synthesized as in Example 2 in 10 ml of toluene, and 0.51 g (5.0 mmol) of triethylamine was added thereto at room temperature. Subsequently, 0.40 g (3.6 mmol) of chlorotrimethylsilane was added dropwise thereto, and stirring was performed at the same temperature for 19 hours. The reaction solution was diluted with 10 ml of toluene, and washing was performed several times with water. The resulting toluene solution was dried over sodium sulfate, and then the solvent was removed by distillation.

The resulting oily residue was dissolved in 10 ml of tetrahydrofuran, and cooling was performed to −60° C. After 0.45 g (4.0 mmol) of potassium tert-butoxide was added to the resulting solution, stirring was performed for 20 minutes. Subsequently, at −50° C., 0.28 g (2.0 mmol) of methyl iodide was added to the mixture, followed by stirring for 25 minutes, and then 0.56 g (2.1 mmol) of diphenylphosphoryl chloride was added thereto, followed by stirring for 1.7 hours. The reaction solution was diluted with 20 ml of toluene, and washing was performed several times using 2.5% aqueous sodium bicarbonate and water under ice cooling. The resulting toluene solution was dried over sodium sulfate, and then the solvent was removed by distillation. The target compound was thereby produced.

REFERENCE EXAMPLE 1

Production of pivaloyloxymethyl(1R, 5S, 6S)-2-[1-(1,3-thiazolin-2-yl)azetidin-3-yl]thio-6-[(1R)-1-hydroxyethyl]-1-methyl-carbapen-2-em-3-carboxylate A solution was prepared by dissolving 0.32 g of an oily residue containing (4R,5R,6S)-6-[(1R)-1-hydroxyethyl]-3-diphenylphosphoryloxy-4-methyl-7-oxo-1-azabicyclo[3.2.0]hept-2-ene-2-carboxylic acid pivaloyloxymethyl ester, which was synthesized as in Example 5 and purified, in 1 ml of acetonitrile, and 0.07 g (0.33 mmol) of a compound represented by formula (18):

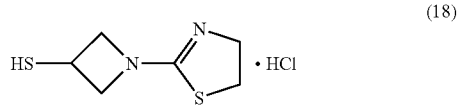

(18)

was added thereto. Subsequently, 0.09 g (0.70 mmol) of diisopropylethylamine was added dropwise thereto at −10° C., and stirring was performed at the same temperature for 3 hours. After the reaction was completed, 20 ml of ethyl acetate and 20 ml of water were added to the reaction solution, and extraction into an aqueous layer was carried out by adding aqueous citric acid, and then extraction into an ethyl acetate layer was carried out by adding 20 ml of ethyl acetate and potassium bicarbonate. The extraction solution was dried over sodium sulfate, and then the solvent was removed by distillation. NMR analysis confirmed the formation of the target compound.

NMR δ (CDCl$_3$): 1.23 (9H, s), 1.23 (3H, d, J=7.1), 1.34 (3H, d-J=6.4 Hz), 3.13-3.21 (1H, m), 3.23 (1H, dd, J=2.7, 6.8 Hz), 3.37 (2H, t, J=7.6 Hz), 3.94-4.03 (4H, m), 4.10-4.26 (3H, m), 4.36-4.42 (2H, m), 5.84 (1H, d, J=5.5 Hz), 5.97 (1H, d, J=5.5 Hz)

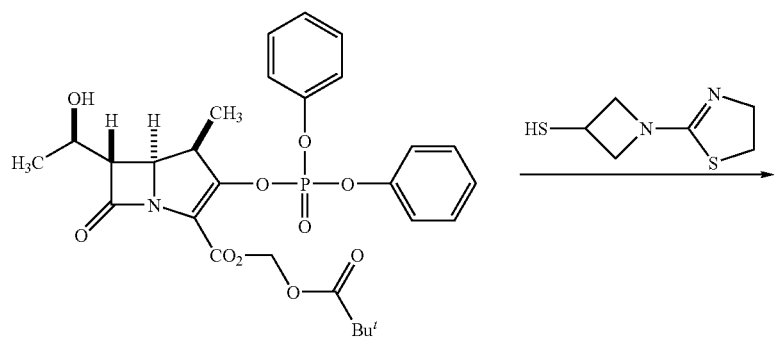

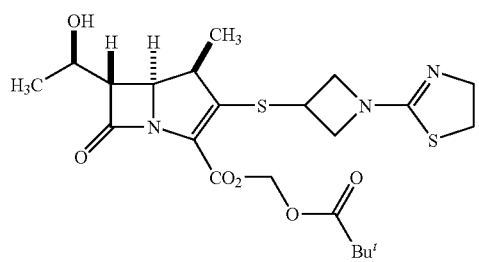

REFERENCE EXAMPLE 2

Production of pivaloyloxymethyl(1R, 5S, 6S)-2-[(3R)-5-oxopyrrolidin-3-yl]thio-6-[(1R)-1-hydroxyethyl]-1-methyl-carbapen-2-em-3-carboxylate

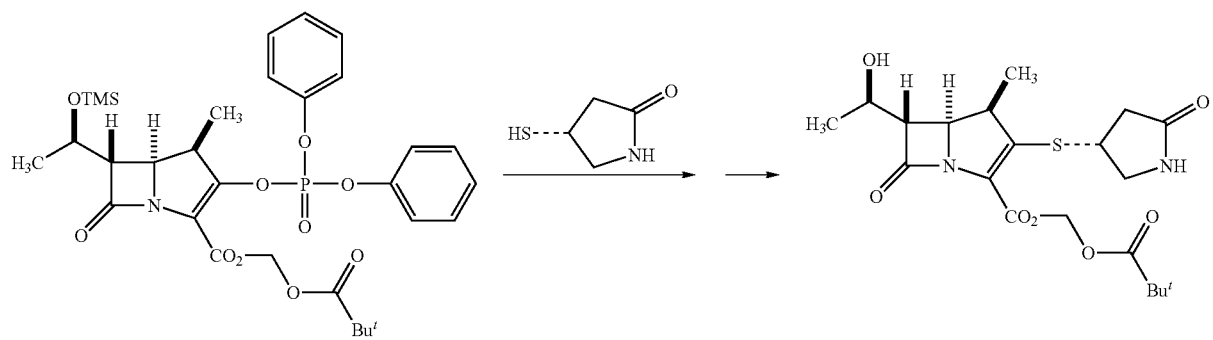

A solution was prepared by dissolving 4.32 g of an oily residue containing (4R, 5R, 6S)-6-[(1R)-1-trimethylsilyloxyethyl]-3-diphenylphosphoryloxy-4-methyl-7-oxo-1-azabicyclo[3.2.0]hept-2-ene-2-carboxylic acid pivaloyloxymethyl ester synthesized as in Example 4 in 15 ml of acetonitrile, and 0.57 g (4.9 mmol) of a compound represented by formula (19):

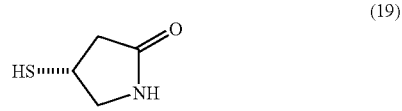

was added thereto. Subsequently, 0.79 g (6.1 mmol) of diisopropylethylamine was added dropwise thereto at 5° C., and stirring was performed at the same temperature for 70 minutes. After the reaction was completed, acetonitrile was removed by distillation. The residue was dissolved in 40 ml of ethyl acetate, and washing was performed several times with aqueous sodium bicarbonate to remove diphenylphosphoric acid which was formed as a by-product. Water was added to the resulting ethyl acetate solution, and 1 N aqueous hydrochloric acid was added thereto to achieve pH 3. The ethyl acetate solution obtained by a separation process was washed with aqueous sodium bicarbonate and water, and then dried over sodium sulfate. The solvent was removed by distillation, and the residue was dissolved in 20 mL of acetone. Toluene (30 mL) was added to the resulting solution, and the acetone solvent was gradually removed by distillation. Formation of a white, turbid solution was confirmed. The white, turbid solution was stirred at 0° C. to 5° C. for 1 hour, and white crystals were obtained by filtration and washing. The white crystals were dissolved in acetone again, and as in the above process, through addition of toluene, removal of the solvent by distillation, stirring, filtration, and washing, 0.70 g of white crystals containing the target compound was obtained.

NMR δ (CDCl$_3$): 1.22 (9H, s), 1.27 (3H, d, J=7.1), 1.32 (3H, d, J 6.3 Hz), 2.39 (1H, dd, J=5.1, 17.1 Hz), 2.83 (1H, dd, J=8.1, 17.1 Hz), 3.26 (1H, dd, J=2.4, 6.8 Hz), 3.31-3.36 (1H, m), 3.84 (1H, dd, J=8.1, 10.7 Hz), 4.01-4.06 (1H, m), 4.22-4.28 (2H, m), 5.82 (1H, d, J=5.5 Hz), 5.96 (1H, d, J=5.5 Hz)

INDUSTRIAL APPLICABILITY

The present invention provides compounds, such as a novel common intermediate (4), and novel precursors thereof (1) and (3), and production processes therefor, which enable efficient synthesis of various 1β-methylcarbapenem compounds for oral administration on which recently research and development has been actively conducted. Thus, the present invention is industrially useful.

In the claims:

1. A process for producing a β-lactam compound comprising protecting the hydroxyl group of a compound represented by formula (1):

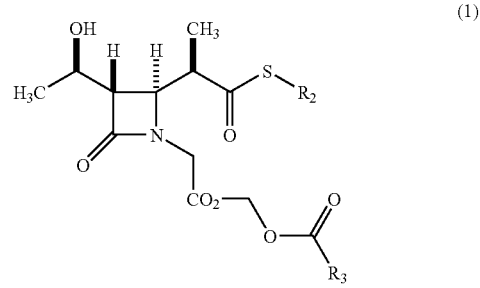

(wherein R$_2$ represents an aryl group or a heteroaryl group; and R$_3$ represents an alkyl group having 1 to 10 carbon atoms or a cycloalkyl group having 3 to 10 carbon atoms), to produce a compound represented by formula (2):

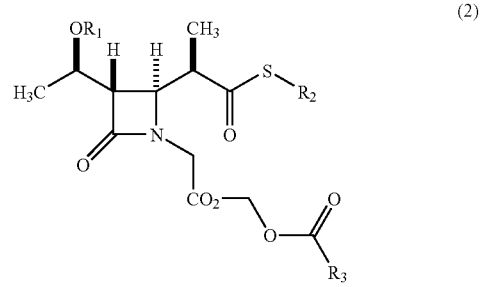

(wherein R$_1$ represents a trimethylsilyl group or a triethylsilyl group; and R$_2$ and R$_3$ are the same as above); cyclizing the compound (2) in the presence of a strong base wherein the strong base is a base selected from the group consisting of an alkali metal alkoxide, an alkali metal amide, and an alkali metal hydride; and subsequently allowing the cyclized compound to react with diphenylphosphoryl chloride to produce a compound represented by formula (3)

(3)

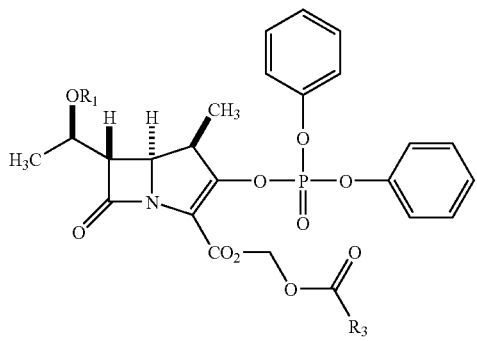

(wherein $R_1$ and $R_3$ are the same as above).

2. The process according to claim 1, wherein the alkali metal alkoxide is potassium tert-butoxide.

3. The process according to claim 1, wherein the alkali metal amide is sodium bis(trimethylsilyl) amide.

4. The process according to claim 1, wherein the alkali metal hydride is sodium hydride.

5. The process according to claim 1, wherein the compound represented by formula (1) is produced by allowing a compound represented by formula (5):

(5)

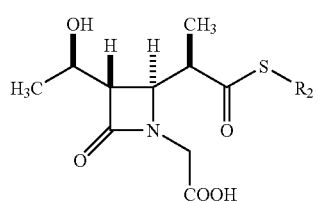

(wherein $R_2$ represents an aryl group or a heteroaryl group), to react with a compound represented by formula (6):

(6)

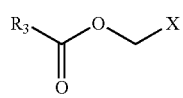

(wherein $R_3$ represents an alkyl group having 1 to 10 carbon atoms or a cycloalkyl group having 3 to 10 carbon atoms; and X represents a halogen atom), in the presence of a base.

6. A process for producing a β-lactam compound represented by formula (4):

(4)

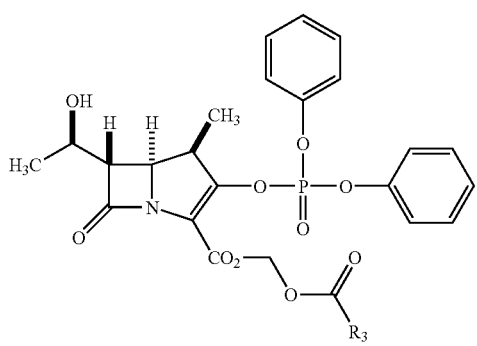

(wherein $R_3$ represents an alkyl group having 1 to 10 carbon atoms or a cycloalkyl group having 3 to 10 carbon atoms), the process comprising deprotecting the hydroxyl moiety of the compound represented by formula (3) produced by the process according to any one of claims 1 and 2-5.

7. A compound represented by formula (1):

(1)

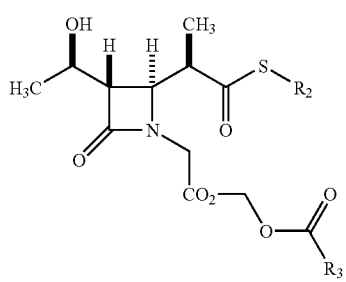

(wherein $R_2$ represents an aryl group or a heteroaryl group; and $R_3$ represents an alkyl group having 1 to 10 carbon atoms or a cycloalkyl group having 3 to 10 carbon atoms).

8. The compound according to claim 7, wherein $R_2$ is a phenyl group or a p-chlorophenyl group.

9. The compound according to claim 7 or 8, wherein $R_3$ is a tert-butyl group.

10. A compound represented by formula (4):

(4)

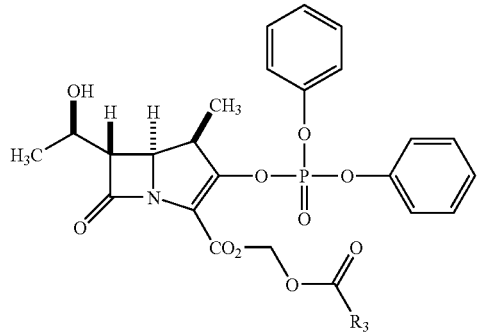

(wherein $R_3$ represents an alkyl group having 1 to 10 carbon atoms or a cycloalkyl group having 3 to 10 carbon atoms).

11. The compound according to claim 10, wherein $R_3$ is a tert-butyl group.

* * * * *